(12) United States Patent
Glode et al.

(10) Patent No.: US 9,922,285 B1
(45) Date of Patent: Mar. 20, 2018

(54) PREDICTIVE ASSIGNMENTS THAT RELATE TO GENETIC INFORMATION AND LEVERAGE MACHINE LEARNING MODELS

(71) Applicant: HumanCode Inc., Denver, CO (US)

(72) Inventors: Christopher M. Glode, Denver, CO (US); Ryan P. Trunck, Denver, CO (US); Rani K. Powers, Broomfield, CO (US); Jennifer L. Lescallett, Sunderland, MD (US)

(73) Assignee: HumanCode, Inc., Denver, CO (US)

( * ) Notice: Subject to any disclaimer, the term of this patent is extended or adjusted under 35 U.S.C. 154(b) by 0 days.

(21) Appl. No.: 15/649,506

(22) Filed: Jul. 13, 2017

(51) Int. Cl.
*G06N 3/04* (2006.01)
*G06N 3/08* (2006.01)
*G06N 5/04* (2006.01)

(52) U.S. Cl.
CPC ............. *G06N 3/08* (2013.01); *G06N 3/0445* (2013.01); *G06N 5/04* (2013.01)

(58) Field of Classification Search
None
See application file for complete search history.

(56) References Cited

U.S. PATENT DOCUMENTS

| | | | | |
|---|---|---|---|---|
| 2002/0077756 | A1* | 6/2002 | Arouh | G01N 33/5091 702/20 |
| 2014/0222349 | A1* | 8/2014 | Higgins | G06F 19/18 702/19 |
| 2016/0364522 | A1* | 12/2016 | Frey | G06F 19/22 |

OTHER PUBLICATIONS

Kelley, David R.; "Basset: learning the regulatory code of the accessible genome with deep convolutional neural networks"; 2016; Cold Spring Harbor Laboratory Press; Genome Res. 2016, 26; pp. 990-999.*

Liu, J., et al. "Genetic variants improve breast cancer risk prediction on mammograms." AMIA . . . Annual Symposium proceedings. AMIA Symposium. vol. 2013. 2013; pp. 876-885.*

Kruppa, Jochen et al.; Risk estimatin and risk prediction using machine-learning methods; 2012; Hum Genet 131:1639-1654.*

Penco, S. et al.; "Assessment of the Role of Genetic Polymorphism in Venous Thrombosis Through Artificial Neural Networks"; 2005; University College London; Annals of Human Genetics 69; pp. 693-706.*

(Continued)

*Primary Examiner* — Stanley K. Hill
(74) *Attorney, Agent, or Firm* — Duft Bornsen & Fettig, LLP; Devin Lee Looijen

(57) ABSTRACT

Systems and methods are provided for performing predictive assignments pertaining to genetic information. One embodiment is a system that includes a genetic prediction server. The genetic prediction server includes an interface that acquires records that each indicate one or more genetic variants determined to exist within an individual, and a controller. The controller selects one or more machine learning models that utilize the genetic variants as input, and loads the machine learning models. For each individual in the records: the controller predictively assigns at least one characteristic to that individual by operating the machine learning models based on at least one genetic variant indicated in the records for that individual. The controller also generates a report indicating at least one predictively assigned characteristic for at least one individual, and transmits a command via the interface for presenting the report at a display.

11 Claims, 11 Drawing Sheets

(56) References Cited

OTHER PUBLICATIONS

Beerenwinkel, Niko et al.; "Diversity and complexity of HIV-1 drug resistance: A bioinformatics approach to predicting phenotype from genotype"; 2002; PNAS vol. 99 No. 13; pp. 8271-8276.*
Kelley, David R. et al.; "Basset: learning the regulatory code of the accessible genome with deep convolutional neural networks"; 2016' Cold Spring Harbor Laboratory Press; pp. 990-999. (Year: 2016).*
Kruppa, Jochen et al.; "Risk estimation and risk prediction using machine-learning methods"; 2012; Springer; Hum Genet (2012) 131:1639-1654. (Year: 2012).*
Anonymous, Wikipedia, "Genome Wide Association Study", https://en.wikipedia.org/wiki/Genome-wide_association_study, retrieved Jun. 23, 2017.
Adit Deshpande, "A Beginner's Guide to Understanding Convolutional Neural Networks", https://adeshpande3.github.io/adeshpande3.github.io/A-Beginner's-Guide-To-Understanding-Convolutional-Neural-Networks/, retrieved Jun. 29, 2017.
Adit Deshpande, "A Beginner's Guide to Understanding Convolutional Neural Networks Par 2", https://adeshpande3.github.io/adeshpande3.github.io/A-Beginner's-Guide-To-Understanding-Convolutional-Neural-Networks-Part-2/, retrieved Jun. 29, 2017.
Romero, Adriana, "Diet Networks: Thin Parameters for Fat Genomics", ICLR Conference paper, arXiv:1611.09340v3 [cs.LG] Mar. 16, 2017, available at https://arxiv.org/pdf/1611.09340.pdf, retrieved Jul. 11, 2017.

* cited by examiner

MANY TO ONE

ONE TO MANY

FIG. 9

| INPUT SOURCE | CATEGORY | RECORDS | SYNC FREQUENCY |
|---|---|---|---|
| SOCIAL NETWORK | SOCIAL & BEHAVIOR | PAGE LIKES, PHOTOS, VIDEOS | HISTORICAL, PERIODIC |
| MICROBLOG | SOCIAL & BEHAVIOR | FOLLOWS, FOLLOWERS, KEYWORDS | HISTORICAL, PERIODIC |
| WORKOUT APP | FITNESS | WORKOUT(PACE, CAL., DIST., HEART RATE, EL., LOC., STEPS), SLEEP | HISTORICAL, PERIODIC |
| WELLNESS APP | HEALTH | EATING HABITS, WORKOUT, SLEEP, STEPS | HISTORICAL, PERIODIC |
| MEDICAL APP | HEALTH | MEDICAL VISITS, INSURANCE CLAIMS, BILLING DATA | HISTORICAL, PERIODIC |
| BANKING APP | FINANCIAL | SPENDING PATTERNS, PURCHASE HISTORY | HISTORICAL, PERIODIC |
| PHOTO APP | SOCIAL & BEHAVIOR | PHOTOS, VIDEOS | HISTORICAL, PERIODIC |
| SMART HOME | SOCIAL & BEHAVIOR | TEMPERATURE, APPLIANCE USAGE | HISTORICAL, PERIODIC |
| BABY MONITOR | SOCIAL & BEHAVIOR | BABY SLEEP PATTERNS, TEMPERATURE, RESTLESSNESS | HISTORICAL, PERIODIC |
| MOBILE DEVICE SENSOR | SOCIAL & BEHAVIOR | LOCATION, MOTION, HEART RATE, STEPS, SLEEP, WORKOUT | ONGOING |
| WEATHER APP | WEATHER | WEATHER HISTORY BY LOCALE | HISTORICAL, PERIODIC |
| PURCHASE HISTORY | FINANCIAL | PURCHASE HISTORY BY CATEGORY | HISTORICAL, PERIODIC |
| VIDEO ON DEMAND | ENTERTAINMENT | PURCHASE AND VIEWING HISTORY | HISTORICAL, PERIODIC |
| APP USAGE | OTHER | WHICH APPLICATIONS, DURATION, TIME, PURCHASE HISTORY | HISTORICAL, PERIODIC |
| OTHER | OTHER | IQ TESTS, PERSONALITY TESTS, ETC. | HISTORICAL, PERIODIC |

900

FIG. 10
CHROMOSOMAL LOCATIONS
FOR GENETIC VARIANTS

| GENETIC VARIANT | CHROMOSOME | POSITION |
|---|---|---|
| SNP 645 | 7 | 1760 |
| SNP 1324 | 5 | 2235 |
| SNP 1261 | 13 | 1921 |
| SNP 13 | 23 | 3519 |
| SEQUENCE 15 | 17 | 0002 |
| SNP 285 | 17 | 7568 |
| SEQUENCE 1354 | 12 | 1232 |
| SNP 72 | 1 | 8734 |

1000

FIG. 11
CATEGORY LOCATIONS FOR
GENETIC VARIANTS

| GENETIC VARIANT | CATEGORY | POSITION |
|---|---|---|
| SNP 645 | METABOLISM | 1 |
| SNP 1324 | METABOLISM | 2 |
| SNP 1261 | SOCIAL | 1 |
| SNP 13 | SOCIAL | 2 |
| SEQUENCE 15 | SOCIAL | 3 |
| SNP 285 | APPEARANCE | 1 |
| SEQUENCE 1354 | APPEARANCE | 2 |
| SNP 72 | APPEARANCE | 3 |

1100

FIG. 12
CATEGORY LOCATIONS FOR
CHARACTERISTICS

| CHARACTERISTIC | CATEGORY | POSITION |
|---|---|---|
| ALLERGIC TO WHEAT | METABOLISM | 1 |
| HIGH CALORIE DIET | METABOLISM | 2 |
| HIGH LIVING TEMP | METABOLISM | 3 |
| HIGHLY CONNECTED | SOCIAL | 1 |
| HIGH FAMILY CONTACT | SOCIAL | 2 |
| WATCHES SITCOMS | SOCIAL | 3 |
| ROUND FACE | APPEARANCE | 1 |
| BROWN EYES | APPEARANCE | 2 |
| SMALL NOSE | APPEARANCE | 3 |

1200

PREDICTIVE ASSIGNMENTS THAT RELATE TO GENETIC INFORMATION AND LEVERAGE MACHINE LEARNING MODELS

FIELD

The disclosure relates to the field of genomics, and in particular, to making predictive assignments that relate to genetic information, and are based on machine learning techniques.

BACKGROUND

The genes of individuals code for a variety of proteins. The expression of a gene in messenger Ribonucleic Acid (mRNA) and protein contributes to a variety of phenotypic traits (i.e., observable traits such as eye color, hair color, etc.) as well as other traits. If a variant occurs in a specific gene, that variation is reflected in mRNA and protein, which can result in a different phenotype. Genetic factors therefore play a major role in a variety of phenotypic traits. For example, normal variations (polymorphisms) in two genes, EDAR and FGFR2, have been associated with differences in hair thickness. Each variation in the nucleotides found in a gene (or the nucleotides that regulate expression of that gene) may be referred to as a genetic variant.

While biological inheritance of physical traits has been studied for decades, associating specific phenotypes with specific genetic variants or combinations thereof remains a complicated process. The human genome itself occupies approximately eighty Gigabytes (GB) of data. Furthermore, there are estimated to be roughly ten million Single Nucleotide Polymorphisms (SNPs) within the genome. Large stretches of the genome include non-coding regions (e.g., introns) as well as coding regions (e.g., exons), and the non-coding regions may regulate how one or more coding regions are expressed. Thus, even variations in non-coding regions may have an impact on phenotype, and false positives may occur when associating a genetic variant with a specific phenotype. Hence, the process of correlating specific genetic variants with specific traits (e.g., specific phenotypes) can be fiendishly complex.

Further compounding the process, it is not possible to identify many traits of an individual without studying the individual closely, and some traits may be hard to precisely quantify (e.g., hair curl, personality, etc.). Some traits may be hard to identify based on the information currently known about the individual. For example, an individual who has constant headaches may be suffering from high blood pressure, high stress, allergies, or other conditions. Without more information, it would be impossible to determine which genetic variants exist within that individual that are correlated with (and/or contribute to) the reported traits or symptoms.

Still further complicating this process, combinations of one or more traits may be linked with one or more genetic variants. Such many-to-many associations between traits and genetic variants remain hard to identify. Hence, those who seek to identify relationships between traits of individuals and the genetic variants found in those individuals continue to seek out enhanced systems and methods for achieving these goals.

SUMMARY

Embodiments described herein utilize machine learning models (e.g., neural networks) that have access to records describing genomic data for individuals, and that also have access to records describing characteristics for individuals. Characteristics may include visual appearance, fitness history, Electronic Health Records (EHRs), travel activities, social network behaviors, digital photo repositories, etc. Using these records, the models may predictively assign characteristics to individuals based on known genetic variants within those individuals, or to predictively assign genetic variants to individuals based on known characteristics of those individuals. Because the models utilize machine learning, the models may further update their predictive logic in response to scoring functions that report whether or not the predictive assignments are accurate.

One embodiment is a system that includes a genetic prediction server. The genetic prediction server includes an interface that acquires records that each indicate one or more genetic variants determined to exist within an individual, and a controller. The controller selects one or more machine learning models that utilize the genetic variants as input, and loads the machine learning models. For each individual in the records: the controller predictively assigns at least one characteristic to that individual by operating the machine learning models based on at least one genetic variant indicated in the records for that individual. The controller also generates a report indicating at least one predictively assigned characteristic for at least one individual, and transmits a command via the interface for presenting the report at a display.

A further embodiment is a method. The method includes acquiring records that each indicate one or more genetic variants determined to exist within an individual, selecting one or more machine learning models that utilize the genetic variants as input, and loading the machine learning models. The method also includes, for each individual in the records, predictively assigning at least one characteristic to that individual by operating the machine learning models based on at least one genetic variant indicated in the records for that individual, generating a report indicating at least one predictively assigned characteristic for at least one individual, and transmitting a command for presenting the report at a display.

A further embodiment is a non-transitory computer readable medium embodying programmed instructions which, when executed by a processor, are operable for performing a method. The method includes acquiring records that each indicate one or more genetic variants determined to exist within an individual, selecting one or more machine learning models that utilize the genetic variants as input, and loading the machine learning models. The method also includes, for each individual in the records, predictively assigning at least one characteristic to that individual by operating the machine learning models based on at least one genetic variant indicated in the records for that individual, generating a report indicating at least one predictively assigned characteristic for at least one individual, and transmitting a command for presenting the report at a display.

Other exemplary embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

FIG. 9 is a table illustrating categorization of characteristics from a variety of input sources in an exemplary embodiment.

FIG. 10 is a table illustrating categorization of genetic variants based on chromosome and position within a chromosome in an exemplary embodiment.

FIG. 11 is a table illustrating categorization of genetic variants into predefined categories in an exemplary embodiment.

FIG. 12 is a table illustrating categorization of characteristics into predefined categories in an exemplary embodiment.

DESCRIPTION

The figures and the following description illustrate specific exemplary embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
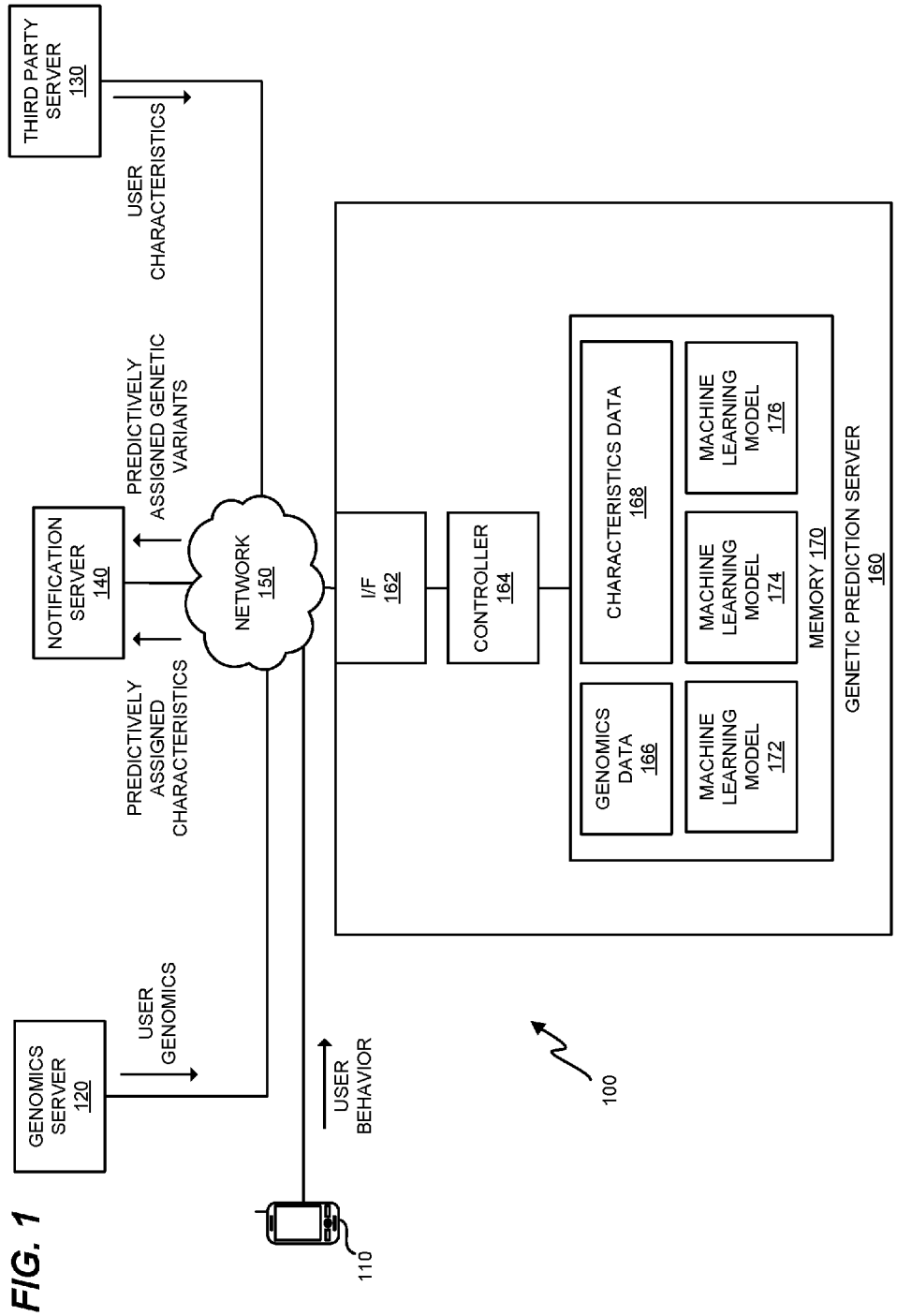
FIG. 1 is a block diagram of a genetic prediction system in an exemplary embodiment.

FIG. 1 is a block diagram of a genetic prediction system 100 in an exemplary embodiment. Genetic prediction system 100 comprises any system, device, or component operable to predictively assign characteristics to individuals based on genetic variants known to exist within those individuals, and/or to predictively assign genetic variants to individuals based on known characteristics for those individuals. In this embodiment, genetic prediction system 100 includes mobile device 110 (e.g., a cellular phone or tablet of a user), genomics server 120, and one or more third party servers 130. These entities provide input via network 150 (e.g., the Internet, a combination of small networks, etc.) to genetic prediction server 160.

Genetic prediction server 160 processes information received from mobile device 110, genomics server 120, and/or third party server 130, and makes predictions relating to the genetics of individuals based on this information. For example, genetic prediction server 160 may predict the characteristics of one or more individuals based on genetic variants known to exist within those individuals, or may predict the genetic variants of individuals based on known characteristics of those individuals.

In this embodiment, genetic prediction server 160 includes multiple components. These components include interface (I/F) 162 and controller 164. I/F 162 receives and transmits data via network 150. I/F 162 may comprise any suitable component for transmitting data, such as an Ethernet port, a wireless transceiver compatible with IEEE 802.11 protocols, etc. Controller 164 manages the operations of genetic prediction server 160 by coordinating the predictive assignment process. Controller 164 may be implemented, for example, as custom circuitry, as a hardware processor executing programmed instructions, or some combination thereof.

Controller 164 stores genomics data 166 in memory 170 based on input from genomics server 120 and/or mobile device 110. Memory 170 may comprise any suitable non-transitory computer readable storage medium, such as a solid state memory, hard disk, etc. Genomics data 166 stores records indicating the genomics of a population of individuals (e.g., millions of individuals). Genomics data 166 includes records that describe genetic variants within specific individuals in the population. For example, each record in genomics data 166 may indicate known genetic variants found within a specific individual, and different records may correspond with different individuals. In a further embodiment, a record in genomics data may report the existence (or non-existence) of a specific genetic variant for a large number of specified individuals. As used herein, the term "genetic variant" refers to a variation of an individual gene (e.g., alleles, Single Nucleotide Polymorphisms (SNPs), etc.), as well as epigenetic variations, variations in nucleotides that regulate gene expression or gene activity, etc.

Controller 164 also stores characteristics data 168 in memory 170 based on input from third party server 130 and/or mobile device 110. As used herein, the "characteristics" of an individual include phenotypes exhibited by an individual, such as hair color, eye color, height, etc. Characteristics also include behaviors of the individual such as fitness patterns, dietary habits, travel patterns, social networking behaviors and preferences (e.g. "Likes" of a sports team or political party), etc. Characteristics may even include the "digital footprint" of an individual, such as interactions with others on a social network, financial transactions performed by the individual, a history of medical treatment for the individual, etc. Various specific characteristics are described below with regard to FIG. 9.

Characteristics data 168 comprises one or more records that indicate characteristics of specific individuals. For example, the records may comprise EHRs or may provide a pulse rate of a user over time during a workout. This information may in turn indicate a characteristic such as a level of cardiovascular health. In other examples, the records may indicate a pattern of purchases of an individual that suggest that the individual has a specific characteristic, such as nearsightedness, acid reflux, or a desire for travel.

Controller 164 utilizes genomics data 166 and/or characteristics data 168 as inputs to machine learning models, and predictively assigns genetic variants and/or characteristics to individuals based on outputs of the machine learning models. In short, machine learning models 172, 174, and 176 are utilized by controller 164 to make predictions pertaining to genetic variants of individuals. Machine learning models 172-176 comprise components that are capable of altering how they process input over time in order to provide more accurate and/or precise output. Machine learning models 172-176 may comprise neural networks, Generative Adversarial Networks (GANs), genetic algorithms, Support Vector Machines, models for Principal component Analysis, Markov Chains, Markov Chain Monte Carlo models, etc. Furthermore machine learning models may be of a plurality of machine learning models, e.g., a neural network connected to principal component analysis. Controller 164 revises machine learning models 172, 174, and 176 based on input indicating an accuracy of predictions made by the machine learning models. These revisions may be dictated by cost functions defined by the machine learning models themselves.

While only three machine learning models are illustrated in FIG. 1, any suitable number of machine learning models may be utilized by genetic prediction server 160. For example, each machine learning model that predicts characteristics may receive one or more genetic variants found within an individual as input, and use this input to predictively assign one or more characteristics to the individual. Similarly, each machine learning model that predicts genetic variants may receive one or more characteristics of an individual as input, and use this data to predictively assign one or more genetic variants of the individual.

Machine learning models stored in memory 170 may be categorized based on whether they are utilized to predict characteristics or to predict genetic variants. Models that are used to predict characteristics may each use a unique set of genetic variants as input, and/or a unique set of characteristics as output. Similarly, models that are used to predict genetic variants may each use a unique set of characteristics as input, and/or a unique set of genetic variants as output. Multiple machine learning models may then be selected by controller 164 to make a variety of predictive assignments pertaining to an individual. In further embodiments, individual machine learning models may utilize inputs and/or outputs that comprise combinations of characteristics and genetic variants for an individual.

Controller 164 also generates reports that indicate the predictively assigned characteristics or genetic variants of specific individuals. A report may be specific to an individual, or may be aggregated data describing an entire population of users. These reports may be provided to notification server 140 for distribution via I/F 162.

Notification server 140 receives reports from genetic prediction server 160 via network 150, and transmits the reports to genomics server 120, third party server 130, and/or one or more mobile devices 110 of individuals. In this manner, reports are provided to those who have an interest in the predictive assignments performed at genetic prediction server 160. For example, an entity operating genomics server 120 may use reports to understand the characteristics of individuals with different genetic variants that have presently unknown effects. Reports may also be useful in aggregate to an entity operating third party server 130 in order to better understand the genetic composition of populations that have certain characteristics. In embodiments where reports correspond with multiple individuals, notification server 140 may anonymize individuals within the reports in order to ensure that privacy is maintained. For example, a third party may receive an aggregated and anonymized report that lists the prevalence of a genetic variant within a population (e.g., without specifying which individuals have been predictively assigned the genetic variant), while a specific person may receive an individualized report that is not anonymized. Reports may also be utilized to develop applications pertaining to genetic prediction server 160, and/or for internal research.

Figure 7:
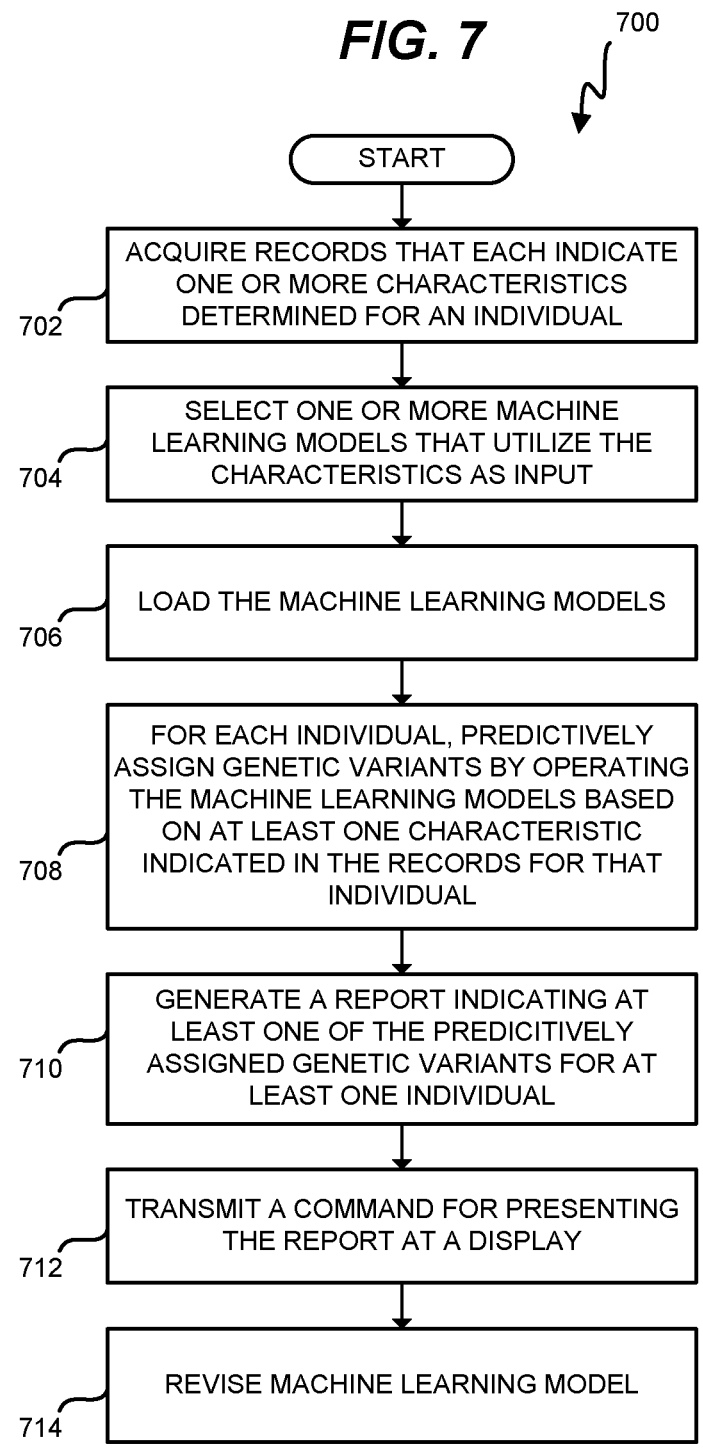
FIG. 7 is a flowchart illustrating a method for operating a genetic prediction system to predictively assign genetic variants to individuals in an exemplary embodiment.
Figure 8:
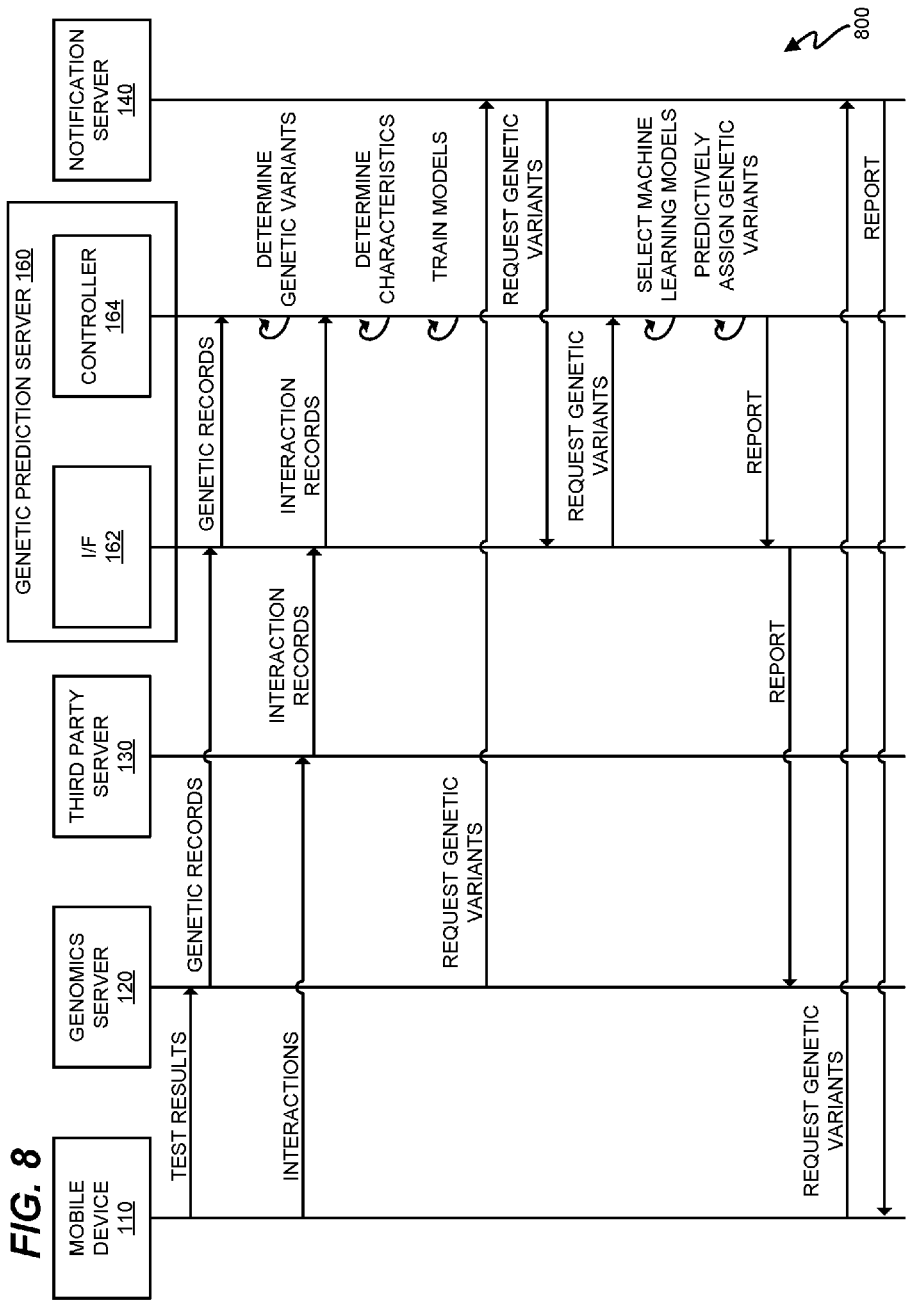
FIG. 8 is a message diagram illustrating communications relating to FIG. 7 in an exemplary embodiment.

With an explanation of the components of genetic prediction system 100 provided above, FIGS. 2-6 delve into details of utilizing genetic prediction system 100 to predict characteristics of individuals based on known genetic variants of those individuals. As used herein, this is referred to as the "forward process." Meanwhile, FIGS. 7-8 illustrate how genetic prediction system 100 may be utilized to predict genetic variants based on characteristics of users. As used herein, this is referred to as the "reverse process."

Forward Process—Predicting Characteristics Based on Genetic Variants

Illustrative details of the operation of genetic prediction system 100 will be discussed with regard to FIG. 2. Assume, for this embodiment, that a genetic testing company operating genomics server 120 desires to determine which characteristics, if any, are associated with specific genetic sequences. The genomics testing company acquires genomics data for a population of individuals, and transmits the genomics data to genetic prediction server 160 in the form of records for processing. These records are provided in order to determine if any characteristics (e.g., phenotypical traits, patterns of behavior, etc.) relate to the genetic sequences. The genomics data is stored in memory (e.g., memory 170).

Figure 2:
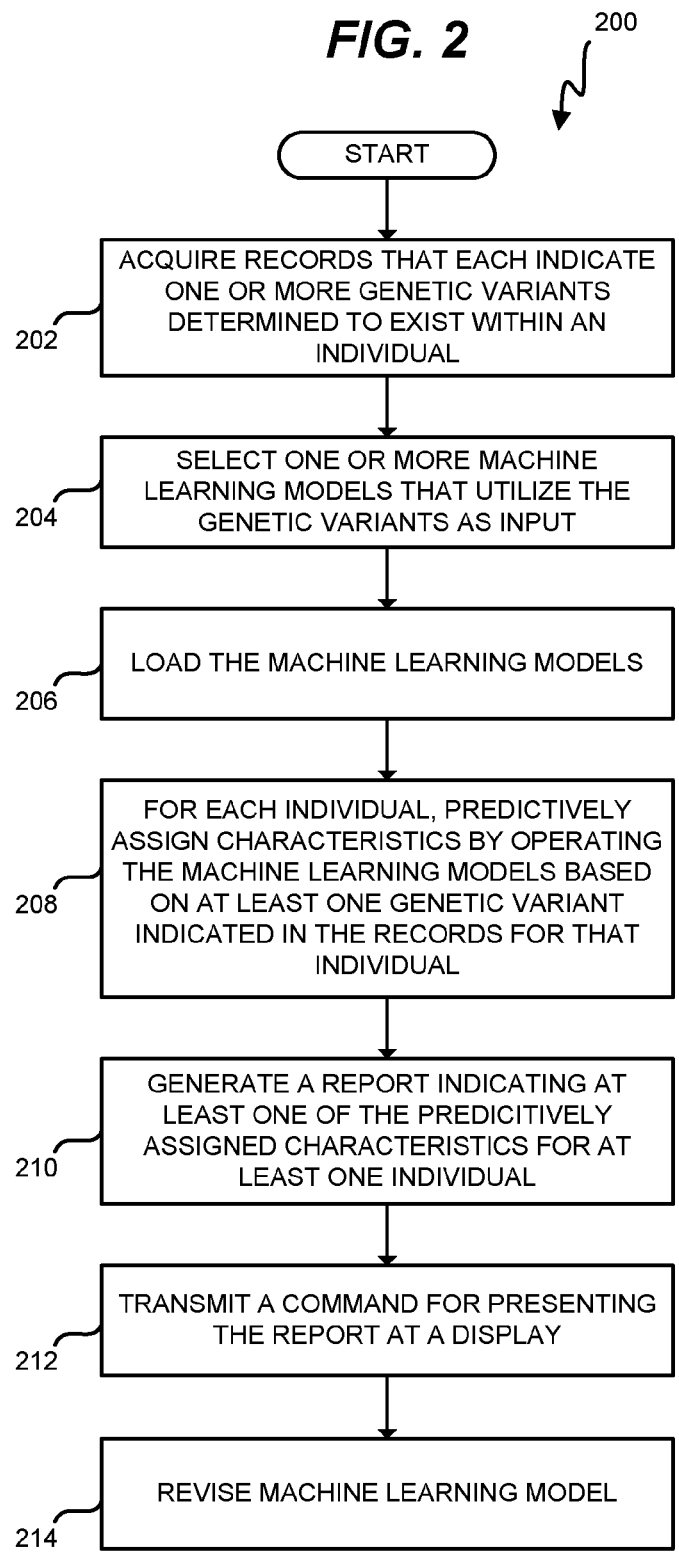
FIG. 2 is a flowchart illustrating a method for operating a genetic prediction system to predictively assign characteristics to individuals in an exemplary embodiment.

FIG. 2 is a flowchart illustrating a method 200 for operating a genetic prediction system 100 to predictively assign characteristics to individuals in an exemplary embodiment. The steps of method 200 are described with reference to genetic prediction system 100 of FIG. 1, but those skilled in the art will appreciate that method 200 may be performed in other systems. The steps of the flowcharts described herein are not all inclusive and may include other steps not shown. The steps described herein may also be performed in an alternative order.

In step 202, genetic prediction server 160 acquires records (e.g., from genomics data 166) that each indicate one or more genetic variants that are determined to exist within an individual. That is, each record indicates one or more genetic variants for at least one individual. The records may correspond with one individual, or with a large number of individuals. In either case, the records indicate determined genetic variants on an individual-by-individual basis.

Controller 164 proceeds to engage in predictive analysis of characteristics, on an individual-by-individual basis. To this end, controller 164 selects one or more machine learning models that utilize the genetic variants as input in step 204. Each machine learning model may utilize a different combination of genetic variants as input. Depending on the records, one or more machine learning models in memory 170 may not have any inputs (i.e., because there is no information in the records about the genetic variants used as inputs by those models). Hence, Controller 164 may selectively prevent machine learning models from being loaded, if the records do not report any genetic variants used as input for these models. This saves processing resources at genetic prediction server 160.

Controller 164 loads the selected machine learning models in step 206, for example by loading the machine learning models from memory 170 into Random Access Memory (RAM). At this point in time, the machine learning models have already been trained using training data sets that indicate known characteristics and known genetic variants of a specific population.

For each individual in the records, controller 164 proceeds to predictively assign characteristics to the individual by operating the loaded machine learning models in step 208. The machine learning models are operated based on at least one genetic variant indicated in the records for the individual being analyzed. For example, the genetic variants indicated in the records for an individual may be used as inputs for the machine learning models for that individual. Controller 164 reviews output from the machine learning models, and predictively assigns characteristics to the individual based on the output. In one embodiment, each output comprises a confidence value associated with a specific characteristic, and controller 164 predictively assigns characteristics based on the confidence values.

Predictively assigned genetic variants and/or characteristics need not be strictly defined by phenotype. That is, genetic prediction server 160 may predictively assign characteristics that are distinct from (i.e., characteristics that do not strictly define) a phenotype defined by known genetic variants of an individual. Genetic prediction server 160 may also predictively assign genetic variants that are distinct from (i.e., genetic variants that do not strictly define) a phenotype defined by the characteristics of an individual. For example, the predictive assignments may be based on much more complex relationships than already-known one-to-one relationships between genes and phenotypes, and may consider behaviors, physical traits, and/or other characteristics that are as-yet not associated with specific genetic variants.

In step 210, controller 164 generates a report indicating at least one of the predictively assigned characteristics for at least one individual. In one embodiment, controller 164 generates a report indicating each predictively assigned characteristic for each individual in the records. For example, the report may indicate predictively assigned characteristics for users of a genetic testing kit.

Controller 164 further transmits a command via I/F 162 for presenting the report via notification server 140 at a display in step 212. The report may then be presented in textual format, as part of a document, etc. as desired by a user operating a display at genomics server 120, third party server 130, and/or an application at mobile device 110.

At some point in time after the report is reviewed, individuals or other entities provide input/feedback indicating whether the predictively assigned characteristics are valid, or are inaccurate. Based on this feedback, controller 164 analyzes each model using a cost function, such as a Mean-Squared Error (MSE) cost function, a cost function that utilizes an L1 penalty function (or other L-norm penalty function), etc. Cost functions may vary between machine learning models, and are also known as scoring functions and/or loss functions. Controller 164 revises each model based on output from the cost function indicating an accuracy of the predictive assignment(s) generated by that model (step 214). In this manner, machine learning models 172-176 adaptively increase in accuracy and precision over time.

Method 200 provides a substantial advantage over prior techniques in that it leverages machine learning models to accurately predict presently unknown characteristics of specific individuals. These predictions may then be utilized to ensure that proper services are provided to the individuals. Similar techniques to those described for method 200 may be utilized for the reverse process.

Figure 3:
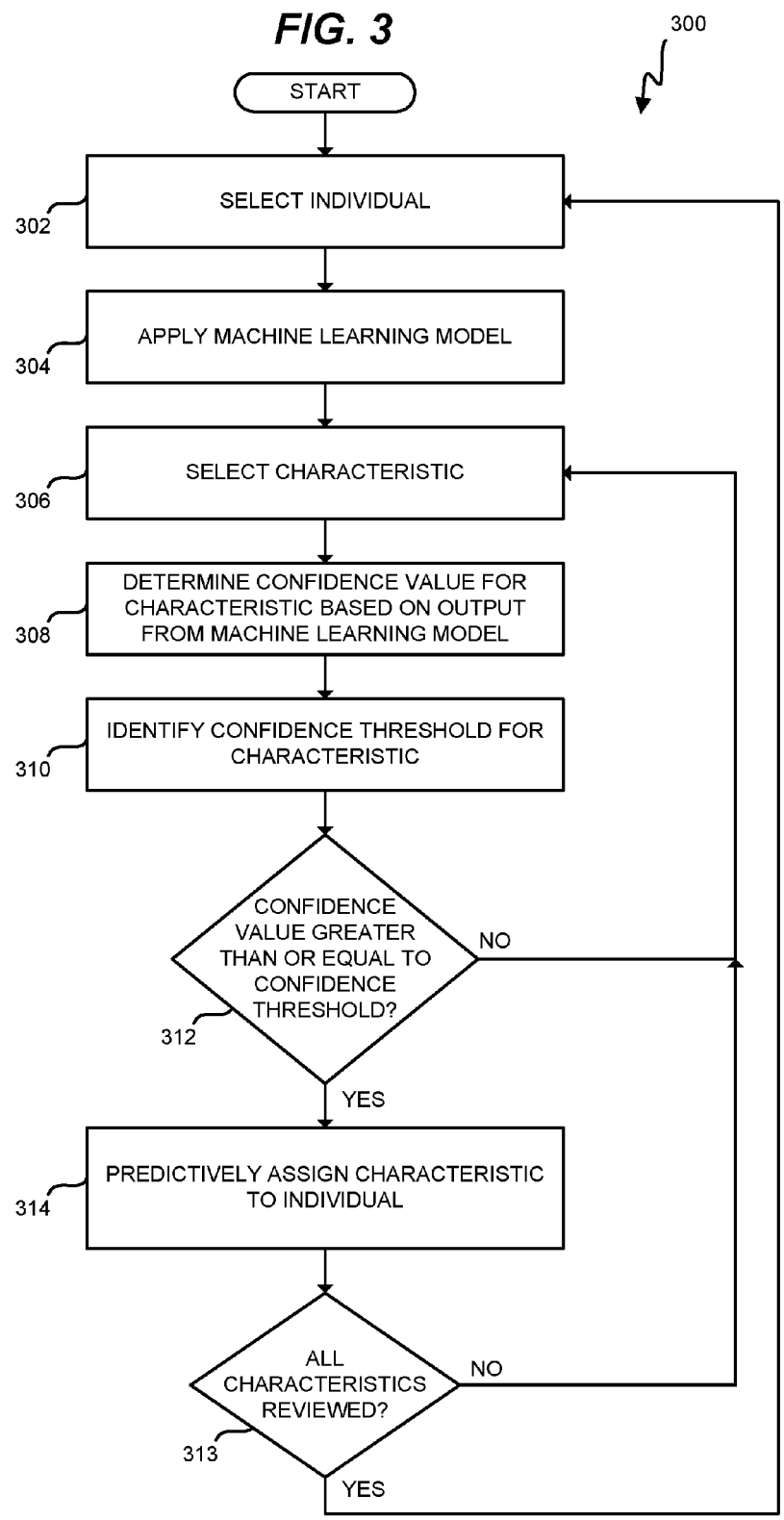
FIG. 3 is a flowchart illustrating a method for determining whether to predictively assign characteristics to individuals, based on output from a machine learning model in an exemplary embodiment.

FIG. 3 is a flowchart illustrating a method 300 for determining whether to predictively assign a characteristic to an individual, based on output from a machine learning model in an exemplary embodiment. Method 300 may be performed, for example, as part of step 208 of method 200 of FIG. 2. FIG. 3 applies to embodiments wherein each output from the machine learning models is a numerical value referred to herein as a "confidence value," and provides a technique by which controller 164 determines whether to predictively assign a characteristic to an individual, based on a confidence value.

According to FIG. 3, controller 164 initiates the predictive assignment process by selecting an individual in step 302. Controller 164 proceeds to select a characteristic in step 304. Controller 164 further applies at least one machine learning model in step 306 in order to acquire confidence values for various characteristics as output, and determines a confidence value for the characteristic based on output from at least one machine learning model in step 308. In embodiments where multiple machine learning models report confidence values for the same characteristic, controller 164 may determine an aggregate confidence value for the characteristic. For example, controller 164 may determine a weighted average of the confidence values, may sum the confidence values, or may perform other operations in order to determine an aggregate confidence value for the characteristic.

In step 310, controller 164 identifies a predefined confidence threshold for the characteristic (e.g., as stored in memory 170). Each characteristic may have a different confidence threshold. This may be valuable when predictively assigning certain types of characteristics to individuals. For example, it may be desirable to predictively assign certain characteristics such as "music lover" at a low confidence threshold, while predictively assigning other characteristics such as "vulnerable to substance addiction" at a high confidence threshold.

Controller 164 proceeds to compare the confidence value to the threshold in step 312. If the confidence value is less than the confidence threshold, controller 164 elects to refrain from predictively assigning the characteristic to the individual. Alternatively, if the confidence value meets or exceeds the predefined confidence threshold for the characteristic, controller 164 predictively assigns the characteristic to the individual (step 314). Controller 164 further determines whether all characteristics have been reviewed for the individual in step 316. If so, controller 164 selects another individual in step 302. If not, controller 164 loops back to select another characteristic in step 306.

While FIG. 3 is described for the forward process, the method of FIG. 3 may be revised to apply to the reverse process as well in order to predictively assign genetic variants based on confidence values and confidence thresholds. The revisions may include iterating through genetic variants instead of characteristics, and using confidence values and confidence thresholds for genetic variants instead of characteristics. Furthermore, in the reverse process, the confidence threshold for different genetic variants may vary. For example, a confidence threshold for a skin cancer allele may be low to ensure that the individual receives screening, while a confidence threshold for a hair color allele may be set to high to ensure that the system does not provide clearly erroneous predictions.

Figure 4:
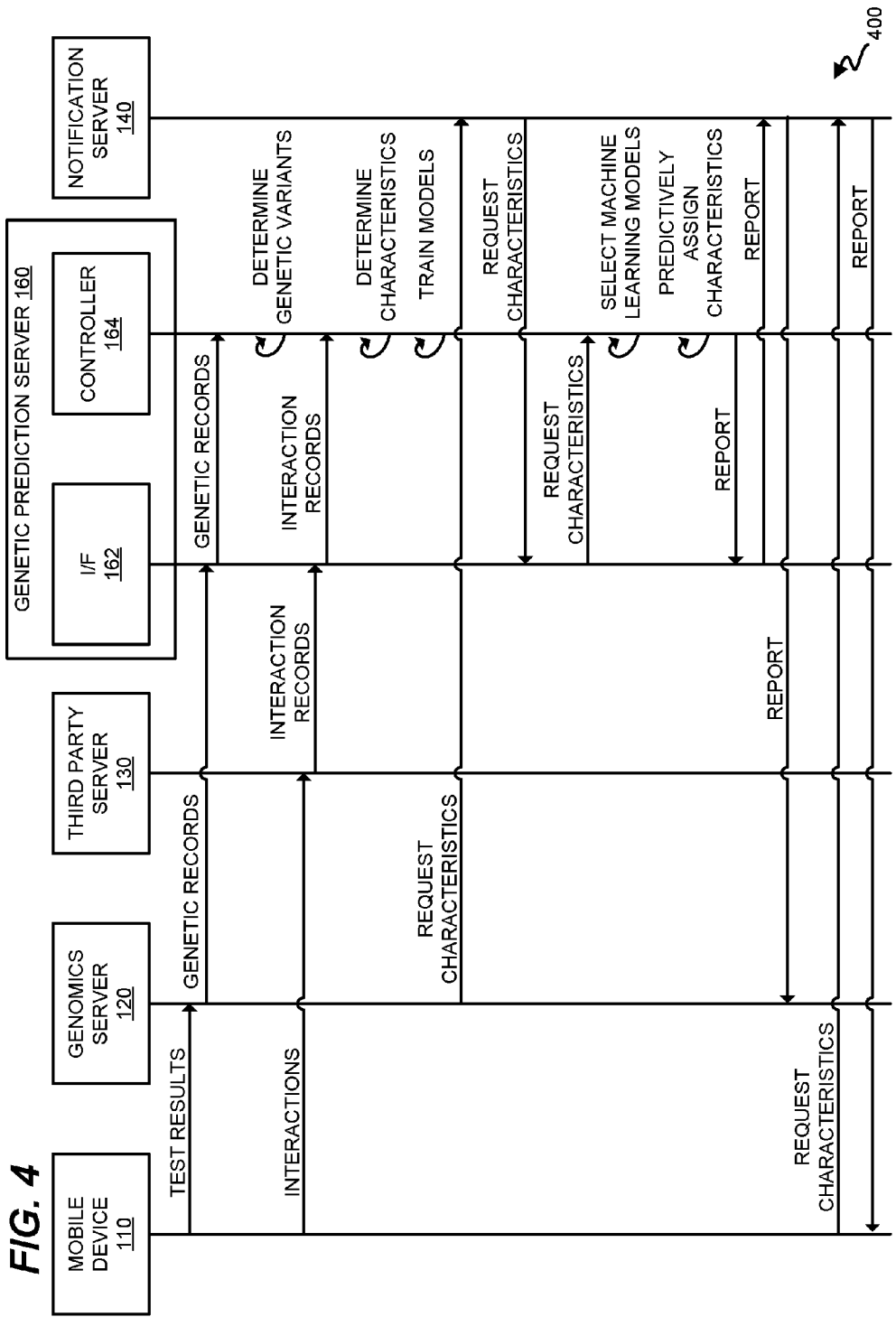
FIG. 4 is a message diagram illustrating communications relating to FIG. 2 in an exemplary embodiment.

FIG. 4 is a message diagram 400 illustrating communications relating to FIG. 2 in an exemplary embodiment. Message diagram 400, as read from top to bottom, illustrates that a user may submit genetic test results for an individual via a mobile device 110 to genomics server 120, which builds records of genetic variants for an individual based on those test results. For example, genomics server 120 may review test results in the form of raw data, and may compile records (e.g., a set of database entries, a table, etc.) that indicate genetic sequences found by the test results. These genetic records are passed to controller 164 via I/F 162. Controller 164 analyzes the results to determine which genetic variants are within each individual.

A mobile device 110 may also be utilized to provide interactions from the user to third party server 130. For example, mobile device 110 may be utilized to indicate a workout history of the individual, may be utilized to create a browsing history of the individual over time, etc. These interactions may be recorded at third party server 130, and interaction records may then be built at third party server 130. In one embodiment, there are multiple third party servers 130, which each correspond with a different application on mobile device 110 (e.g., a fitness app, banking app, etc.). Interaction records are provided to genetic prediction server 160, and controller 164 determines characteristics of the individual based on the interaction records. These characteristics are not predictively assigned, but rather are known characteristics indicated by the records.

As interaction records and genetic records are received for individuals, controller 164 updates memory (e.g., memory 170) with new genomics data 166 and characteristics data 168. At this point in time, no predictions have taken place.

As genomics data 166 and characteristics data 168 are aggregated over time for multiple individuals, controller 164 may proceed to use the aggregated data to train and/or revise one or more of machine learning models 172-176. For example, in an embodiment where machine learning models 172-176 comprise neural networks, genomics data 166 and characteristics data 168 may be utilized as training data sets to provide initial weights to connections between nodes in the neural network. At some point in time, genomics server 120 (or third party server 130, or mobile device 110) requests a report that predictively assigns characteristics to an individual. That is, the request is for a prediction of characteristics (e.g., as-yet unknown characteristics of the individual), based on known genetic variants found in the individual (e.g., via testing). The request is received at notification server 140, which forwards the request to genetic prediction server 160.

Controller 164 proceeds to load known genetic variants of the individual, and use these genetic variants as input to one or more machine learning models stored in memory 170. Controller 164 then generates a report indicating each predictively assigned characteristic of the individual, and provides that report to notification server 140. Notification server 140 then transmits the report to the entity that initially requested the report.

If additional requests for reports for the individual are provided, and no new information exists for the individual, then notification server 140 may return a copy of the report instead of forwarding the request onward to genetic prediction server 160. Alternatively, if new genetic records are received for the individual and an additional request for a report is provided, notification server 140 may forward the request onward to genetic prediction server 160. Controller 164 may then operate the machine learning models again to update the report, using the new information.

If new interaction records are received that indicate new characteristics of the individual, controller 164 may utilize this information to score the output of the machine learning models, and update the models. For example, in embodiments where the machine learning models comprise neural networks, controller 164 may revise weights between nodes of the neural networks based on a cost function associated with each neural network. This allows for non-linear mapping and identification of complex relationships between genetic variants and characteristics (e.g., behaviors) of individuals.

Neural Networks

Figure 5:
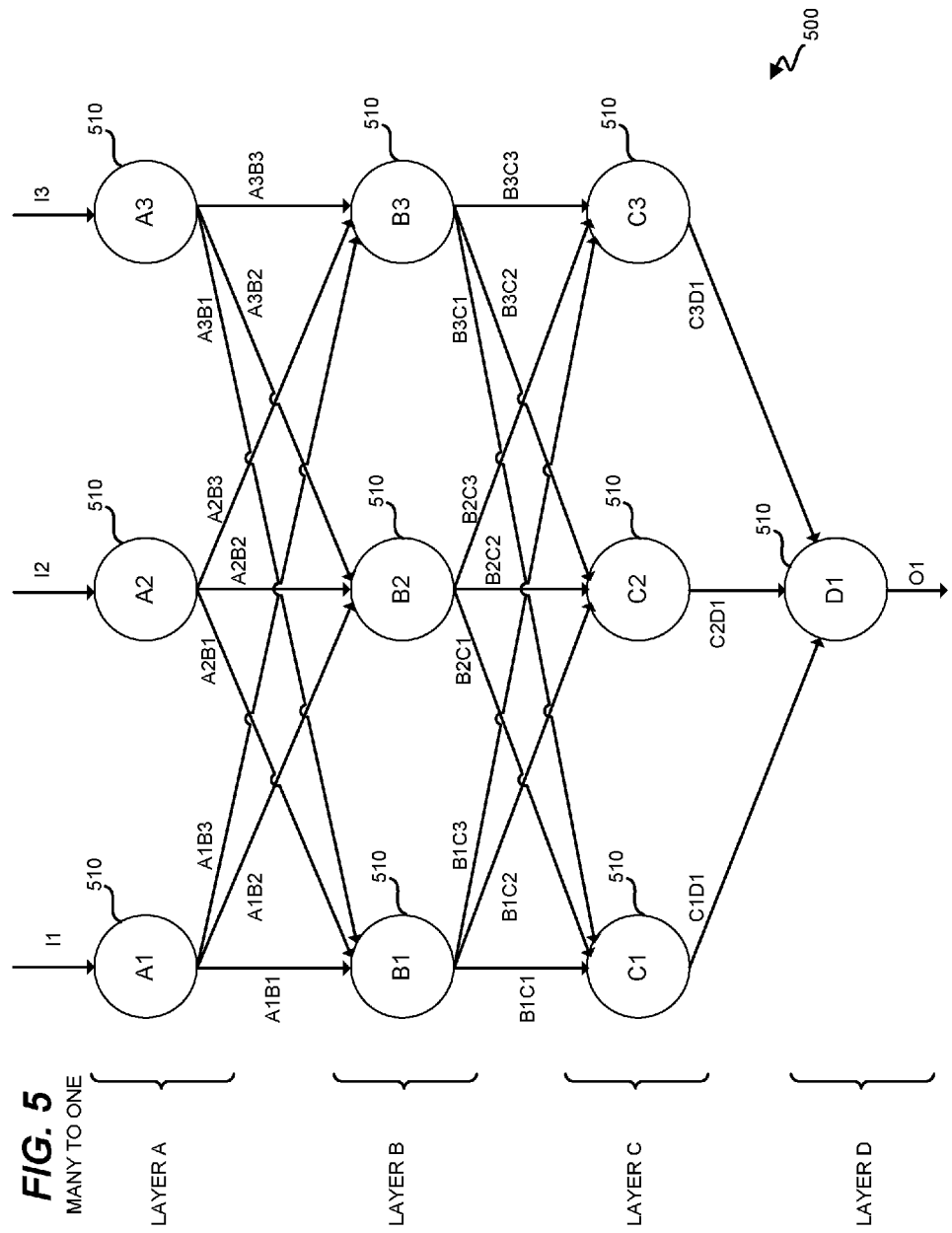
FIGS. 5-6 illustrate neural networks that facilitate predictive assignments in an exemplary embodiment.
Figure 6:
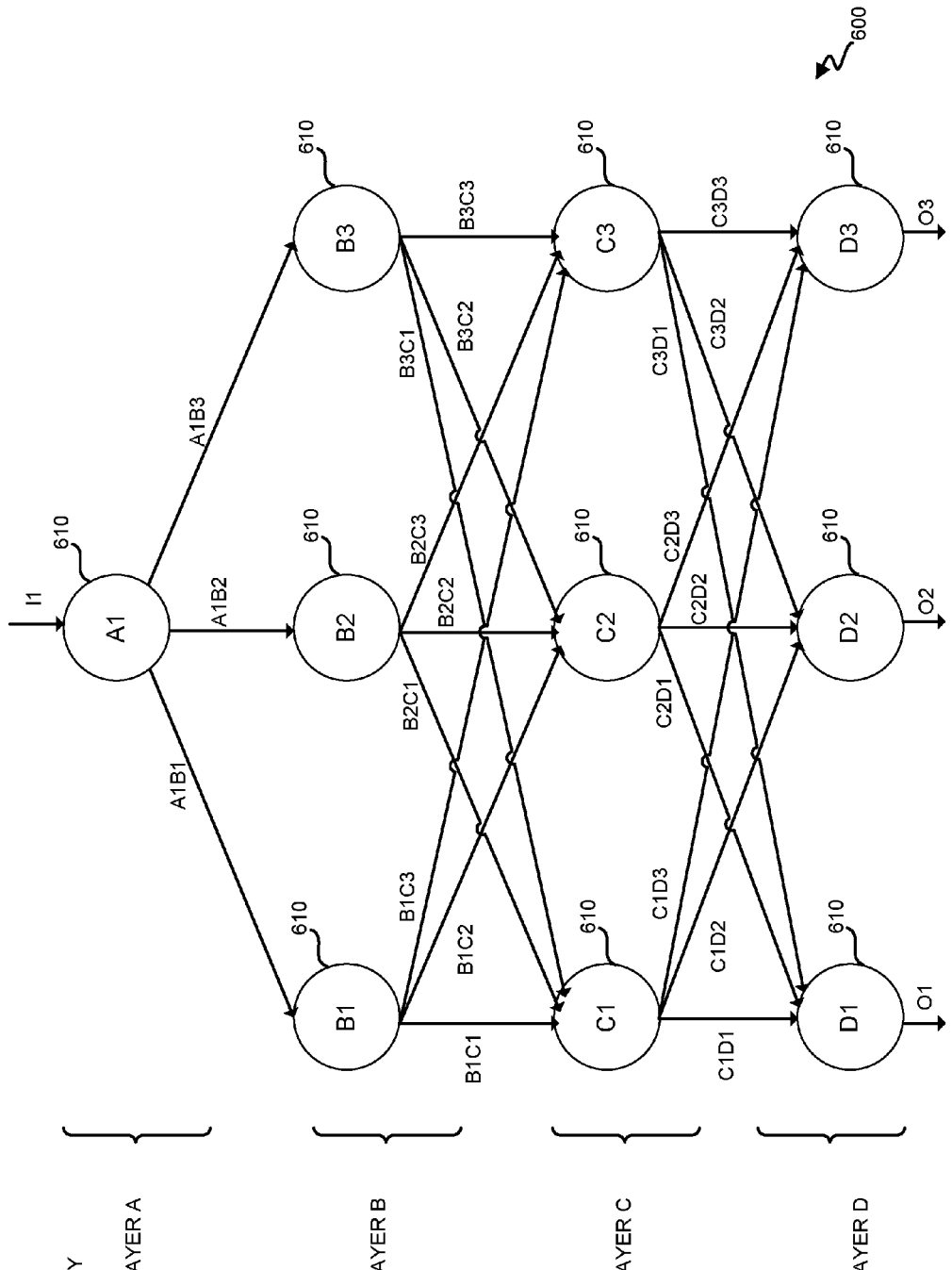

FIGS. 5-6 illustrate neural networks that facilitate predictive assignments in an exemplary embodiment. While these neural networks are described for the forward process, similar architectures may also be used for the reverse process. Furthermore, the architectures illustrated herein have been simplified in order to facilitate understanding. In further embodiments, any suitable number of layers (e.g., hundreds or thousands of layers), nodes per layer, and types of layer may be utilized in order to facilitate processing.

FIG. 5 illustrates a neural network 500 that utilizes many known genetic variants within an individual to predictively assign a single output characteristic to an individual. Neural network 500 includes multiple layers (e.g., layer A, layer B, layer C, layer D), and each layer includes one or more nodes 510 (e.g., A1-A3, B1-B3, C1-C3, D1). Furthermore, nodes 510 in neural network 500 are coupled via weighted connections. Each weighted connection is labeled starting with a source node, and ending with a destination node. Thus, the weighted connection between node A1 and node B1 is referred to as "A1B1." The strength of a weighted connection indicates how much influence input received from the source node will have upon the destination node, and may for example be indicated by a numerical value between zero and one. A weighted connection may also be referred to as a "synaptic weight" or "link weight."

In this embodiment, neural network 500 is illustrated as having three fully connected layers (layer A, layer B, layer C), wherein each source node is connected with each destination node in the next layer. Layer A is the top layer, and receives known genetic variants as input. Neural network 500 also includes a summation layer (layer D), which comprises a bottom layer that provides an output indicating a characteristic.

Each node 510 in layer A receives input indicating whether a different genetic variant exists within the individual. For example, node A1 may receive input I1 indicating a first SNP, node A2 may receive input I2 indicating a nucleotide sequence, and node A3 may receive input I3 indicating a second SNP. Based on this input, each node 510 provides input to one or more connected nodes 510 in the next layer. For example, input regarding a specific SNP for an individual may cause node A1 to provide input along connection A1B1 which is strongly weighted, while also providing input along connection A1B3 which has a weak connection weight. Eventually, input travels to node D1, which is associated with the characteristic of "high metabolism." The output O1 of node D1 may be a binary result indicating whether the characteristic exists, or may be a numerical value (e.g., a percentage, or a value between one and zero) indicating a likelihood that the characteristic exists.

In further embodiments, any suitable number of nodes may be used in each layer, and any suitable number and type of layers may be utilized. In some embodiments, entire groups of summation, fully connected, and/or convolutional layers may be grouped together such that they are sequentially located with respect to each other within the neural network. Furthermore, the layers need not all be fully connected layers. For example, convolutional layers (e.g., in the upper layers), summation layers, hidden layers, etc. may be utilized as desired.

In embodiments where convolutional layers are used, inputs to the neural network, such as genetic variants (or characteristics, for the reverse process) may be grouped together, assigned locations (e.g., dimensional coordinates) relative to each other along an axis, and convolved. In such embodiments, genetic variants may be categorized and located/positioned based on the types of physical traits or mental traits they provide. For example, genetic variants may be assigned categories of metabolism, socialization, fitness, perception, etc., and may be assigned a specific location (e.g., dimensional coordinate) within the category with respect to other genetic variants in that category. In a further embodiment, genetic variants may be grouped into the same category and provided with a dimensional coordinate in that category based on their physical location in the same gene, physical location on the same chromosome, pertinence to a specific aspect of health, etc.

If N axes of categorization are utilized, the coordinate for a genetic variant may have N dimensions. These dimensional coordinates may therefore be 1D, 2D, 3D, etc., and convolution may be applied across one or more of these dimensions depending on the architecture of the neural network.

For the reverse process, characteristics may be categorized based on traits such as metabolism, socialization, fitness (or any other suitable categories) and assigned a dimensional coordinate. This relational ordering facilitates convolution of inputs at the neural network as discussed above. It also may help to reduce the amount of noise in the neural network.

FIG. 6 illustrates a further neural network 600 wherein one input genetic variant (I1) is utilized to predict multiple characteristics of a user as output (O1, O2, O3). Because the confidence value in predicting a characteristic for a user based on a single genetic variant exhibited by that user is low, results for the same characteristic from multiple neural networks (each corresponding with a different input genetic variant) may be combined in order to provide an aggregate value, based upon which controller 164 decides whether or not to predictively assign the characteristic. In this embodiment, neural network 600 includes multiple layers of nodes 610, and neural network 600 may vary in design in the same manner as described above for neural network 500.

In further embodiments, neural networks utilized by controller 164 in machine learning models 172-176 may be structured to allow for inputs and/or outputs that include combinations of characteristics and/or genetic variants. This may further enhance the accuracy of predictively assignment performed via genetic prediction system 100. However, it may remain beneficial to limit the number of inputs and outputs at each neural network in order to reduce the amount of noise encountered by each neural network when performing predictive assignment.

Neural networks 500 and 600 provide a substantial benefit for predictive assignment, because they enable large amounts of data (and many different types of data) to be leveraged for large populations in order to make multiple indirect connections between genetic variants and characteristics. These connections would not be noticeable to an individual human searching through such vast amounts of data. For example, a neural network may utilize many subtle, weak connections between behaviors and genetic variants in order to arrive at conclusive results indicating the presence of a specific genetic variant.

While neural networks 500 and 600 may be utilized in the forward process described above, neural networks having a similar architecture may be utilized in the reverse process, wherein output genetic variants are predictively assigned to an individual based on known input characteristics.

Neural network 500 and neural network 600 may further be implemented as recurrent neural networks or feedforward networks as desired. In one embodiment, neural network 500 and neural network 600 include features that reduce the likelihood of overfitting. These features may involve regularization via cost function, analysis of a confidence interval of output from the neural network, etc. In further embodiments, the number of inputs or outputs at each neural network may be restricted to a limited number (e.g., five, or one), and these inputs or outputs may be chosen via pre-processing techniques. For example, a reduction in input features for a neural network ensures that there are fewer features than training data points. This in turn helps to prevent overfit scenarios.

In another embodiment, the number of input features for a neural network is reduced through learning or pre-processing the input data to a feature embedding. A feature embedding may be generated through parameter prediction networks. Compared to a fully connected layer, this process will significantly reduce the number of parameters for the neural network. For example, a neural network could learn a function that maps a large number of input features to a much smaller number of features using random projections, per class histograms, etc.

Reverse Process—Predicting Genetic Variants Based on Characteristics

While FIGS. 2-4 discuss the forward process and FIGS. 5-6 discuss neural network architectures, an explanation of the reverse process is provided in FIGS. 7-8.

FIG. 7 is a flowchart illustrating a method 700 for operating a genetic prediction system to predictively assign genetic variants to individuals in an exemplary embodiment. FIG. 7 utilizes similar techniques to FIG. 2, but engages in the reverse process instead of the forward process. That is, method 700 uses stored characteristics data 168 in order to predict genetic variants of individuals.

Assume, for this embodiment, that individuals are requesting reports that will predictively assign the individuals specific genetic variants, based on behavioral patterns and/or other characteristics of the individuals. These predictive assignments may be utilized to make inferences about genotype information for users where only phenotype information is available. This could be useful for a variety of purposes ranging from further genomic imputation (e.g. by determining that a user is a tall European male and therefore has genotypes that are correlated with other genotypes, which themselves are further correlated with a testable condition (e.g. high blood pressure).

In step 702, controller 164 acquires records that each indicate one or more characteristics determined for an individual. In step 704, controller 164 selects one or more machine learning models that utilize one or more of the characteristics as input. Controller 164 may, for example, select machine learning models that receive multiple characteristics as input, so long as at least one input characteristic for each selected model is provided in the records. Controller 164 may forego the selection of machine learning models that do not use any of the indicated characteristics as input in order to save processing resources.

Controller 164 further loads the machine learning models (e.g., into RAM) in step 706. For each individual in the records, controller 164 predictively assigns one or more genetic variants to the individual in step 708. This predictive assignment is performed by operating the machine learning models based on the characteristics indicated in the records for that individual. These operations may be performed, for example, via reverse process versions of the neural networks described in FIGS. 5-6, and in a similar manner as described in FIGS. 2-3.

In step 710, controller 164 generates a report indicating one or more predictively assigned genetic variants for at least on individual, and in step 712 controller 164 operates I/F 162 to transmit a command for presenting the report at a display (e.g., a display for third party server 130, genomics server 120, mobile device 110, etc.). The command may comprise, for example, a packetized message that includes the report. Controller 164 further revises the machine learning models, in response to input indicating an accuracy of the predictive assignments (step 714).

FIG. 8 is a message diagram 800 illustrating communications relating to FIG. 7 in an exemplary embodiment. Message diagram 800 illustrates that genetic prediction server 160 may predictively assign genetic variants to individuals based on a request from a third party, such as genomics server 120, third party server 130, mobile device 110, etc., and may generate reports for use by that third party based on stored machine learning models.

If additional requests for reports are provided, and no new information exists for the individual, then notification server 140 may send a copy of the report instead of utilizing the machine learning models again. However, if new interaction records are received for the individual and an additional request for a report is provided, controller 164 may operate the machine learning models again to update the report, using the new information. Furthermore, if new genetic records are received that indicate new genetic variants of the individual, controller 164 may utilize this information to score the output of the machine learning models, and update the models. For example, in embodiments where the machine learning models comprise neural networks, controller 164 may revise weights between nodes of the neural networks based on a score from a cost function associated with each neural network.

Various discussions of components and methods for genetic prediction system 100 have been provided above. Further discussion focuses upon input sources that may be utilized by genetic prediction server, as well as how characteristics for an individual may be determined based on data from various input sources. These determined characteristics may then be utilized to predict genetic variants of individuals, or to revise machine learning models that predict characteristics of individuals.

Input Sources and Categorization

FIG. 9 is a table 900 illustrating categorization of characteristics from a variety of input sources in an exemplary embodiment. Specifically, table 900 illustrates multiple input sources, categories that may be assigned to interaction records from those input sources, and types of records that may be acquired from the input sources. Table 900 further illustrates a synchronization frequency at which interaction records may be retrieved from the input sources. As used in table 900, a "historical" synchronization is a backward-looking synchronization that may pull in all available records (e.g., across all of time). Thus, a historical synchronization may be performed by controller 164 once prior to regular, periodically performed synchronizations. A periodic synchronization may occur regularly at predefined intervals, such as once per hour, once per day, once per week, once per month, etc. Furthermore, periodic synchronizations may pull back records generated since the last periodic synchronization. This helps to ensure that bandwidth at network 150 is efficiently utilized by genetic prediction server 160. An "ongoing" synchronization provides updates as soon as new records are generated. Thus, ongoing updates for a mobile device sensor may constantly report location of an individual as the individual moves throughout the day.

Interaction records such as those illustrated in FIG. 9 may be retrieved in large batches for use by genetic prediction server 160, and these batches may comprise records for large numbers of individuals (e.g., thousands or hundreds of thousands of individuals).

Controller 164 may analyze interaction records from any of the variety of input sources provided in table 900, and may determine that the records indicate specific characteristics about users. Controller 164 may consult guidelines stored in memory 170, analyze the records, and determine characteristics for an individual based on those guidelines. For example, if an individual works out for more than thirty minutes in a day at a rate of more than four times a week, controller 164 may apply the characteristic of "physically active" to the individual. This determined characteristic may then be utilized as one or many inputs to the machine learning models in order to predictively assign genetic variants to the user. In a further embodiment, a neural network that precedes machine learning models 172-176 may be utilized to determine characteristics based on interaction records of individuals. A lasso may also be utilized for this process.

FIGS. 10-12 illustrate how genetic variants and characteristics may be categorized in an exemplary embodiment. Specifically, FIG. 10 is a table 1000 illustrating categorization of genetic variants based on chromosome and position within a chromosome in an exemplary embodiment, and FIG. 11 is a table 1100 illustrating categorization of genetic variants into predefined categories in an exemplary embodiment. FIG. 12 is a table 1200 illustrating categorization of characteristics into predefined categories in an exemplary embodiment. In this embodiment, characteristics and/or genetic variants may be grouped into categories and assigned positions so that entire categories of characteristics may be convolved together by a convolutional layer of a neural network as desired.

EXAMPLES

In the following examples, additional processes, systems, and methods are described in the context of a genetic prediction system 100 that utilizes machine learning models. In these examples, genetic prediction server 160 acquires data that enables predictive assignments for large numbers of individuals, as well as personalized predictive assignments performed on a person-by-person basis.

In this example, controller 164 operates I/F 162 to acquire interaction records from a social network, interaction records from a workout app, interaction records from a video on demand app, and interaction records for smart home devices. These interaction records are retrieved as batches of records from servers for the various input sources mentioned above. The interaction records are received (e.g., for an individual upon login of the individual, in bulk, etc.), but each interaction record is associated with a specific individual. Thus, when the records are received in bulk, they may correspond with thousands or hundreds of thousands of different individuals. Each individual may have different types of records associated therewith. Controller 164 periodically retrieves the interaction records, determines characteristics of individuals by analyzing the interaction records based on guidelines stored in memory 170 in order to build characteristics data 168.

Controller 164 also builds genomics data 166 by retrieving genetic records from one or more genomics servers 120. For example, controller 164 may retrieve genetic records from genomics servers of different companies that provide different genetic tests. In this example, the genomics records are provided en masse, based on whether individuals have opted in to predictive assignment or not.

Having built genomics data 166 and characteristics data 168, controller 164 proceeds to correlate individuals in the characteristics data with individuals in the genomics data. For example, a user may opt-in to account linking by providing credentials that link genomic records with interaction records. In a further example, if both genomics data 166 and characteristics data 168 refer to individuals that have the same name and birth date, or the same unique identifier, then controller 164 may determine that these individuals are one and the same. In this manner, controller 164 determines known genetic variants and known characteristics of individuals. Assume, for this embodiment, that a third party that operates a workout app for users wishes to know more about its user base, and transmits a request to genetic prediction server 160 to predictively assign characteristics to users of the workout app that have undergone voluntary genetic testing.

In this example, machine learning models 172-176 have already been trained based on a vetted set of training data. Thus, for the forward process, controller 164 begins to iterate through individuals. For a first individual, controller 164 determines that the individual has genetic variants referred to as SNP A, SNP B, and nucleotide sequence C. Controller 164 reviews the machine learning models. Controller 164 determines that machine learning model 172 utilizes SNP A as input, and machine learning model 174 uses SNP B and nucleotide sequence C as input, and machine learning model 176 utilizes none of these genetic variants as input. Thus, controller 164 loads machine learning model 172 and machine learning model 174 into RAM, and ignores machine learning model 176.

Controller 164 uses the genetic variants of the individual as inputs to the loaded machine learning models, and receives outputs indicating characteristics of the individual. The outputs are the characteristics of "socially active" at a confidence value of 0.05, "physically active" at a confidence values of 0.65, and "high metabolism" at a confidence value of 0.90. The confidence threshold for the "socially active" characteristic is 0.60, the confidence threshold for "physically active" is 0.35, and the confidence threshold for "high metabolism" is 0.80. Based on this information, controller 164 predictively assigns characteristics of physically active and high metabolism to the individual. Controller 164 then proceeds to the next individual until the users of the workout app have been analyzed.

Controller 164 generates a report which is provided to the third party via notification server 140. The report indicates characteristics of individuals that use the workout app and have opted in to predictive assignment. The report applies characteristics to each of the individuals. The third party then provides a personalized suggestion of a product to the individuals.

For the reverse process, a user is aware of the physical appearance of their grandparent, and wishes to know which genetic variants their grandparent may have. To this end, the user requests a report predicting genetic variants of the grandparent, based on known characteristics of the grandparent. Thus, controller 164 engages in the reverse process.

Controller 164 first accesses memory 170 to confirm that the user is allowed receive predictive assignments for the grandparent. Controller 164 further identifies known characteristics of the grandparent such as a wheat allergy, a poorly performing short term memory, a dislike of sugary foods, and highly social behaviors. Controller 164 identifies six machine learning models that utilize at least one of these characteristics as input. Controller 164 loads the machine learning models into memory, operates the machine learning models based on the input, and receives output from the machine learning models. Two of the machine learning models indicate a genetic variant known as SNP 622, which is associated with Alzheimer's disease. One of the machine learning models indicates SNP 974 which is associated with allergies to shellfish. SNP 622 is output with a confidence value of 0.58 and 0.28, while SNP 974 is reported with a confidence value of 0.66. Controller performs a weighted average of the confidence values for SNP 622, weighting the first output to be twice as valuable as the second output. This arrives at a confidence interval of 0.48. The confidence threshold for SNP 974 is 0.3, and the confidence threshold for SNP 622 is 0.1. The confidence threshold for SNP 974 is set relatively low to ensure monitoring of the grandparent for Alzheimer's-like tendencies when the grandparent grows older, while the confidence threshold for SNP 622 is set very low to ensure that the grandparent may be monitored for a potentially life-threatening condition. Note that these genetic variants were not yet checked for in any genetic test, and these genetic variants have been predictively assigned based on characteristics that are not strongly associated therewith.

Controller 164 compares the confidence values against the confidence thresholds, and predictively assigns SNP 622 and SNP 974 to the grandparent. Controller 164 generates a report, which is transmitted via I/F 162 to notification server 140, and from notification server 140 to the user. The user then displays the report at mobile device 110. Based on the report, the user schedules an additional genetic test to check for SNP 622, and takes the grandparent to a follow-up medical visit to test for shellfish allergies. Results indicate that the grandparent does not have SNP 622, but does have a shellfish allergy.

Figure 13:
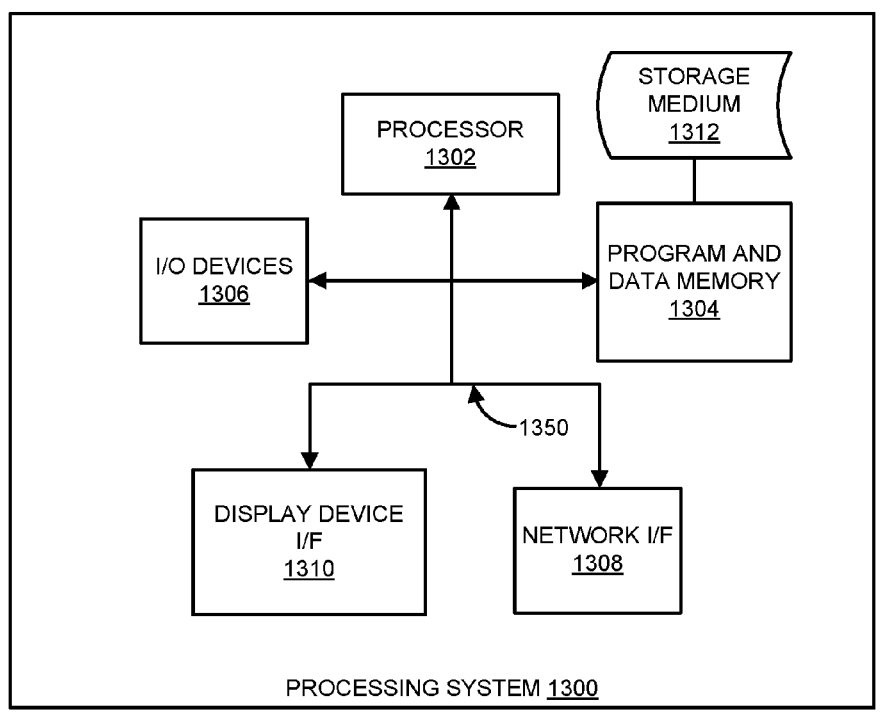
FIG. 13 illustrates an exemplary processing system operable to execute programmed instructions embodied on a computer readable medium.

Embodiments disclosed herein can take the form of a hardware processor implementing programmed instructions, as hardware, as firmware operating on electronic circuitry, or various combinations thereof. In one particular embodiment, software is used to direct a processing system of mobile device 110, genetic prediction server 160 and/or notification server 140 to perform the various operations disclosed herein. FIG. 13 illustrates an exemplary processing system 1300 operable to execute a computer readable medium embodying programmed instructions. Processing system 1300 is operable to perform the above operations by executing programmed instructions tangibly embodied on computer readable storage medium 1312. In this regard, embodiments of the invention can take the form of a computer program accessible via computer readable medium 1312 providing program code for use by a computer (e.g., processing system 1300) or any other instruction execution system. For the purposes of this description, computer readable storage medium 1312 can be anything that can contain or store the program for use by the computer (e.g., processing system 1300).

Computer readable storage medium 1312 can be an electronic, magnetic, optical, electromagnetic, infrared, or semiconductor device, or other non-transitory computer readable medium. Examples of computer readable storage medium 1312 include a solid state memory, a magnetic tape, a removable computer diskette, a random access memory (RAM), a read-only memory (ROM), a rigid magnetic disk, and an optical disk. Current examples of optical disks include compact disk—read only memory (CD-ROM), compact disk—read/write (CD-R/W), and DVD.

Processing system 1300, being used for storing and/or executing the program code, includes at least one processor 1302 coupled to program and data memory 1304 through a system bus 1350. Program and data memory 1304 can include local memory employed during actual execution of the program code, bulk storage, and cache memories that provide temporary storage of at least some program code and/or data in order to reduce the number of times the code and/or data are retrieved from bulk storage during execution.

Input/output or I/O devices 1306 (including but not limited to keyboards, displays, pointing devices, etc.) can be coupled either directly or through intervening I/O controllers. Network adapter interfaces 1308 can also be integrated with the system to enable processing system 1300 to become coupled to other data processing systems or storage devices through intervening private or public networks. Modems, cable modems, IBM Channel attachments, SCSI, Fibre Channel, and Ethernet cards are just a few of the currently available types of network or host interface adapters. Display device interface 1310 can be integrated with the system to interface to one or more display devices, such as printing systems and screens for presentation of data generated by processor 1302.

What is claimed is:

1. A system comprising:
   a genetic prediction server comprising:
      an interface that acquires records that each indicate one or more genetic variants determined to exist within an individual; and
      a controller that selects one or more machine learning models that utilize genetic variants as input, loads the one or more machine learning models, assigns a dimensional coordinate to each genetic variant used as an input to the one or more machine learning models, and for each individual in the records: predictively assigns at least one characteristic to that individual by operating the one or more machine learning models, utilizing at least one genetic variant indicated in the records for that individual as input to the one or more machine learning models, wherein
      each of the one or more machine learning models comprises a multi-layer neural network, each layer comprising multiple nodes, nodes in different layers are coupled via weighted connections, each node in an input layer of a neural network corresponds with a genetic variant, each node in an output layer of a neural network corresponds with a characteristic, and each neural network includes a convolutional layer that convolves about genetic variants that are used as input for the neural network, based on the dimensional coordinates of genetic variants;
      the controller generates a report indicating at least one predictively assigned characteristic for at least one individual, and transmits a command via the interface for presenting the report at a display,
      the controller analyzes input indicating accuracy of a predictively assigned characteristic, and determines a score for one of the one or more machine learning models based on the analyzed input and a cost function, and
      the controller revises the weighted connections based on the cost function for each neural network.

2. The system of claim 1 wherein:
   for each individual, the one or more machine learning models predictively assign characteristics to the individual that are distinct from a phenotype that is defined by genetic variants that are already indicated in the records for that individual.

3. The system of claim 1 wherein:
   the controller determines a confidence value for each characteristic based on output from the one or more machine learning models, compares the confidence value to a confidence threshold for that characteristic, and predictively assigns a characteristic to an individual if the confidence value for that characteristic exceeds the confidence threshold for that characteristic.

4. The system of claim 1 wherein:
   each machine learning model corresponds with a different characteristic; and
   each machine learning model utilizes a different combination of genetic variants as input.

5. A method comprising:
   acquiring records that each indicate one or more genetic variants determined to exist within an individual;
   selecting one or more machine learning models that utilize genetic variants as input;
   loading the one or more machine learning models;
   for each of the one or more machine learning models, assigning a dimensional coordinate to each genetic variant used as an input to that machine learning model;
   for each individual in the records, predictively assigning at least one characteristic to that individual by operating the one or more machine learning models, utilizing at least one genetic variant indicated in the records for that individual as input to the one or more machine learning models, wherein each of the one or more machine learning models comprises a multi-layer neural network, each layer comprising multiple nodes, nodes in different layers are coupled via weighted connections, each node in an input layer of a neural network corresponds with a genetic variant, each node in an output layer of a neural network corresponds with a characteristic, and each neural network includes a convolutional layer that convolves about genetic variants, based on the dimensional coordinates of genetic variants;
   generating a report indicating at least one predictively assigned characteristic for at least one individual;
   transmitting a command for presenting the report at a display;
   analyzing input indicating accuracy of a predictively assigned characteristic;
   determining a score for one of the one or more machine learning models based on the analyzed input and a cost function; and
   revising the weighted connections based on the cost function.

6. The method of claim 5 wherein:
   for each individual, the one or more machine learning models predictively assign characteristics to the individual that are distinct from a phenotype that is defined by genetic variants that are already indicated in the records for that individual.

7. The method of claim 5 further comprising:
   determining a confidence value for each characteristic based on output from the one or more machine learning models;
   comparing the confidence value to a confidence threshold for that characteristic; and predictively assigning a characteristic to an individual if the confidence value for that characteristic exceeds the confidence threshold for that characteristic.

8. The method of claim 5 wherein:

each machine learning model corresponds with a different characteristic; and each machine learning model utilizes a different combination of genetic variants as input.

9. A non-transitory computer readable medium embodying programmed instructions which, when executed by a processor, are operable for performing a method comprising:

acquiring records that each indicate one or more genetic variants determined to exist within an individual;

selecting one or more machine learning models that utilize genetic variants as input;

loading the one or more machine learning models;

for each of the one or more machine learning models, assigning a dimensional coordinate to each genetic variant used as an input to that machine learning model;

for each individual in the records, predictively assigning at least one characteristic to that individual by operating the one or more machine learning models, utilizing at least one genetic variant indicated in the records for that individual as input to the one or more machine learning models, wherein each of the one or more machine learning models comprises a multi-layer neural network, each layer comprising multiple nodes, nodes in different layers are coupled via weighted connections, each node in an input layer of a neural network corresponds with a genetic variant, each node in an output layer of a neural network corresponds with a characteristic, and each neural network includes a convolutional layer that convolves about genetic variants, based on the dimensional coordinates of genetic variants;

generating a report indicating at least one predictively assigned characteristic for at least one individual;

transmitting a command for presenting the report at a display;

analyzing input indicating accuracy of a predictively assigned characteristic;

determining a score for one of the one or more machine learning models based on the analyzed input and a cost function; and revising the weighted connections based on the cost function.

10. The medium of claim 9 wherein:

for each individual, the one or more machine learning models predictively assign characteristics to the individual that are distinct from a phenotype that is defined by genetic variants that are already indicated in the records for that individual.

11. The medium of claim 9 wherein the method further comprises:

determining a confidence value for each characteristic based on output from the one or more machine learning models;

comparing the confidence value to a confidence threshold for that characteristic; and predictively assigning a characteristic to an individual if the confidence value for that characteristic exceeds the confidence threshold for that characteristic.

* * * * *